US011873838B2

(12) United States Patent
Bothma

(10) Patent No.: US 11,873,838 B2
(45) Date of Patent: *Jan. 16, 2024

(54) BLOWER FOR BREATHING APPARATUS

(71) Applicant: Fisher & Paykel Healthcare Limited, Auckland (NZ)

(72) Inventor: Johannes Nicolaas Bothma, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 85 days.

This patent is subject to a terminal disclaimer.

(21) Appl. No.: 17/304,067

(22) Filed: Jun. 14, 2021

(65) Prior Publication Data

US 2021/0301832 A1 Sep. 30, 2021

Related U.S. Application Data

(63) Continuation of application No. 15/106,669, filed as application No. PCT/IB2014/067201 on Dec. 22, 2014, now Pat. No. 11,073,165.

(Continued)

(51) Int. Cl.
*F04D 29/44* (2006.01)
*A61M 16/00* (2006.01)
(Continued)

(52) U.S. Cl.
CPC ....... *F04D 29/444* (2013.01); *A61M 16/0066* (2013.01); *F04D 17/16* (2013.01); *F04D 17/164* (2013.01); *F04D 17/165* (2013.01); *F04D 25/06* (2013.01); *F04D 25/0606* (2013.01); *F04D 29/281* (2013.01); *F04D 29/30* (2013.01); *F04D 29/4206* (2013.01); *F04D 29/663* (2013.01); *F04D 29/667* (2013.01);
(Continued)

(58) Field of Classification Search
CPC .......... A61M 16/0066; A61M 2206/14; A61M 2206/16; A61M 2206/20; A61M 2206/12; A61M 2205/42; F04D 29/444; F04D 17/16; F04D 29/663; F04D 29/4206; F04D 29/667; F04D 29/281; F04D 25/0606; F04D 17/164; F04D 17/165; F04D 29/30; F04D 29/448; F05D 2250/52
USPC ................ 415/208.2–208.4, 211.1
See application file for complete search history.

(56) References Cited

U.S. PATENT DOCUMENTS 2,576,700 A 11/1951 Heinrich
3,861,826 A 1/1975 Dean
(Continued)

FOREIGN PATENT DOCUMENTS

CN 1174942 3/1998
CN 1975175 6/2007
(Continued)

OTHER PUBLICATIONS

International Search Report; PCT/IB2014/067201; dated Mar. 30, 2015; 6 pages.

*Primary Examiner* — Justine R Yu
*Assistant Examiner* — Alexander Morales
(74) *Attorney, Agent, or Firm* — Knobbe Martens Olson & Bear, LLP

(57) ABSTRACT

A blower for a breathing apparatus has a diffuser for increasing static pressure and/or reducing noise and/or mitigating pressure instabilities and/or managing reverse flow.

17 Claims, 18 Drawing Sheets

Related U.S. Application Data

(60) Provisional application No. 61/920,014, filed on Dec. 23, 2013.

(51) Int. Cl.
    *F04D 29/28*     (2006.01)
    *F04D 25/06*     (2006.01)
    *F04D 17/16*     (2006.01)
    *F04D 29/30*     (2006.01)
    *F04D 29/42*     (2006.01)
    *F04D 29/66*     (2006.01)

(52) U.S. Cl.
    CPC ..... *A61M 2205/42* (2013.01); *A61M 2206/14* (2013.01); *F05D 2250/52* (2013.01)

(56) References Cited

U.S. PATENT DOCUMENTS

| | | | |
|---|---|---|---|
| 4,824,325 A * | 4/1989 | Bandukwalla | F04D 29/444 |
| | | | 415/208.4 |
| 4,859,145 A | 8/1989 | Sidransky | |
| 5,344,285 A | 9/1994 | O'Sullivan et al. | |
| 5,516,263 A | 5/1996 | Nishida | |
| 5,573,374 A | 11/1996 | Giberson | |
| 5,619,612 A | 4/1997 | Glucksman | |
| 6,558,117 B1 | 5/2003 | Fukaya | |
| 7,223,070 B2 * | 5/2007 | Tam | F04D 29/626 |
| | | | 415/211.2 |
| 8,016,557 B2 | 9/2011 | Abdelwahab et al. | |
| 8,267,648 B2 | 9/2012 | Kenyon et al. | |
| 9,420,829 B2 | 8/2016 | Thorens | |
| 11,073,165 B2 | 7/2021 | Bothma | |
| 2002/0064460 A1 | 5/2002 | Chien | |
| 2005/0111974 A1 | 5/2005 | Loringer | |
| 2008/0014080 A1 | 1/2008 | Fang | |
| 2008/0310978 A1 | 12/2008 | Hoffman | |
| 2013/0251560 A1 | 9/2013 | Xue et al. | |
| 2013/0280060 A1 * | 10/2013 | Nasir | F04D 29/444 |
| | | | 415/208.2 |
| 2014/0069432 A1 * | 3/2014 | Mebasser | F04D 29/403 |
| | | | 128/205.25 |
| 2014/0308119 A1 * | 10/2014 | Harada | F03B 3/02 |
| | | | 415/208.2 |
| 2017/0002830 A1 | 1/2017 | Bothma | |

FOREIGN PATENT DOCUMENTS

| | | |
|---|---|---|
| CN | 101608631 | 12/2009 |
| CN | 103185027 | 7/2013 |
| CN | 103321922 | 9/2013 |
| EP | 3673941 | 7/2020 |
| GB | 205112 | 1/1924 |
| JP | 2009-030552 | 2/2009 |
| NZ | 577485 A | 1/2011 |
| WO | WO 2013/009193 | 1/2013 |

* cited by examiner

BLOWER FOR BREATHING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to a blower for a breathing apparatus, and in particular to a blower with a diffuser for increasing static pressure and/or reducing noise and/or mitigating pressure instabilities and/or managing reverse flow.

SUMMARY OF INVENTION

It is an object of the present invention to provide a blower with improved static pressure and/or a blower that manages reverse flow.

In one aspect the present invention may be said to consist in blower for a breathing apparatus comprising: a housing with an inlet and outlet, a motor within the housing for rotating an impeller, a diffuser within the housing between the impeller and outlet, the diffuser comprising a plate with (planar) diffuser elements, wherein the diffuser elements are arranged in cascades on the plate, each cascade comprising a series of diffuser elements.

Preferably each diffuser element is offset from adjacent diffuser elements in the cascade.

Preferably the diffuser elements in each cascade are arranged spirally from the perimeter to the centre of the diffuser plate.

Preferably the diffuser elements are aerofoils.

Preferably the blower further comprises a circumferential diffuser elements arranged proximate the perimeter of the diffuser plate to direct airflow from the perimeter of the impeller to the planar diffuser elements.

Preferably the planar diffuser elements in a cascade spiral from a corresponding circumferential diffuser element towards the centre of the diffuser plate.

In another aspect the present invention may be said to consist in a blower for a breathing apparatus comprising: a housing with an inlet and outlet, a motor within the housing for rotating an impeller, a diffuser within the housing between the impeller and outlet, the diffuser comprising one or more circumferential rings with circumferential diffuser elements are arranged on the ring(s) to direct air to an outlet.

Preferably the diffuser elements are arranged in cascades on the ring(s), each cascade comprising a series of diffuser elements.

Preferably each diffuser element is offset from adjacent diffuser elements in the cascade.

Preferably the diffuser element cascades are arranged on the inner surface of the one or more rings surrounding the impeller and optionally wherein for each cascade the diffuser elements are arranged in a helical manner.

Preferably the diffuser elements are aerofoils.

Preferably the blower comprises an annular ramped wall around the impeller to reduce flutter.

In another aspect the present invention may be said to consist in a blower according to any paragraph above with multiple diffusers and impellers.

In another aspect the present invention may be said to consist in a blower for a breathing apparatus comprising: a housing with an inlet and outlet, a motor within the housing for rotating an impeller, a diffuser within the housing between the impeller and outlet, the diffuser comprising diffuser elements, wherein the diffuser elements are arranged in cascades, each cascade comprising a series of diffuser elements.

Also described is a blower for a breathing apparatus comprising: a housing with an inlet and outlet, a motor within the housing for rotating an impeller, and a diffuser within the housing between the impeller and the outlet, the diffuser comprising aerofoil diffuser elements.

Preferably the diffuser elements are arranged in cascades, each cascade comprising a series of diffuser elements offset from adjacent diffuser elements in the cascade.

Preferably the diffuser element cascades are arranged on a diffuser plate parallel to the impeller, and optionally arranged spirally from the perimeter to the centre of the diffuser plate.

Preferably the blower further comprises circumferential diffuser elements arranged proximate the perimeter of the diffuser plate to direct airflow from the perimeter of the impeller to the diffuser elements.

Preferably each spirally arranged cascade spirals from a corresponding circumferential diffuser element to the centre of the diffuser plate.

Preferably the diffuser comprises a circumferential ring around the impeller, and the diffuser elements are arranged on the ring that directs air to an outlet.

Preferably the diffuser elements are arranged in cascades, each cascade comprising a series of diffuser elements, wherein each diffuser element in the cascade is offset from adjacent diffuser elements in the cascade.

Preferably the diffuser element cascades are arranged on the inner surface of one or more rings surrounding the impeller and optionally wherein for each cascade the diffuser elements are arranged in a helical manner.

Preferably a blower is provided as above with multiple diffusers and impellers.

In embodiments, diffuser elements redirect reverse flow such that the reverse flow moves in the same direction as forward flow. This helps to reduce blade pass noise caused by pressure instabilities. When the reverse flow reaches the volute in which the impeller sits, it is substantially moving in the same direction as the forward flow and can easily join the stream. Otherwise, a 'whirring' sound can be heard because reverse flow moving in the opposite direction causes motor slowing/stalling.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. The invention consists in the foregoing and also envisages constructions of which the following gives examples only.

BRIEF DESCRIPTION OF THE DRAWINGS

Preferred embodiments of the invention will be described with reference to the drawings, of which.

DETAILED DESCRIPTION OF PREFERRED EMBODIMENTS

Axial Inlet/Axial Outlet Embodiment

Figure 1:
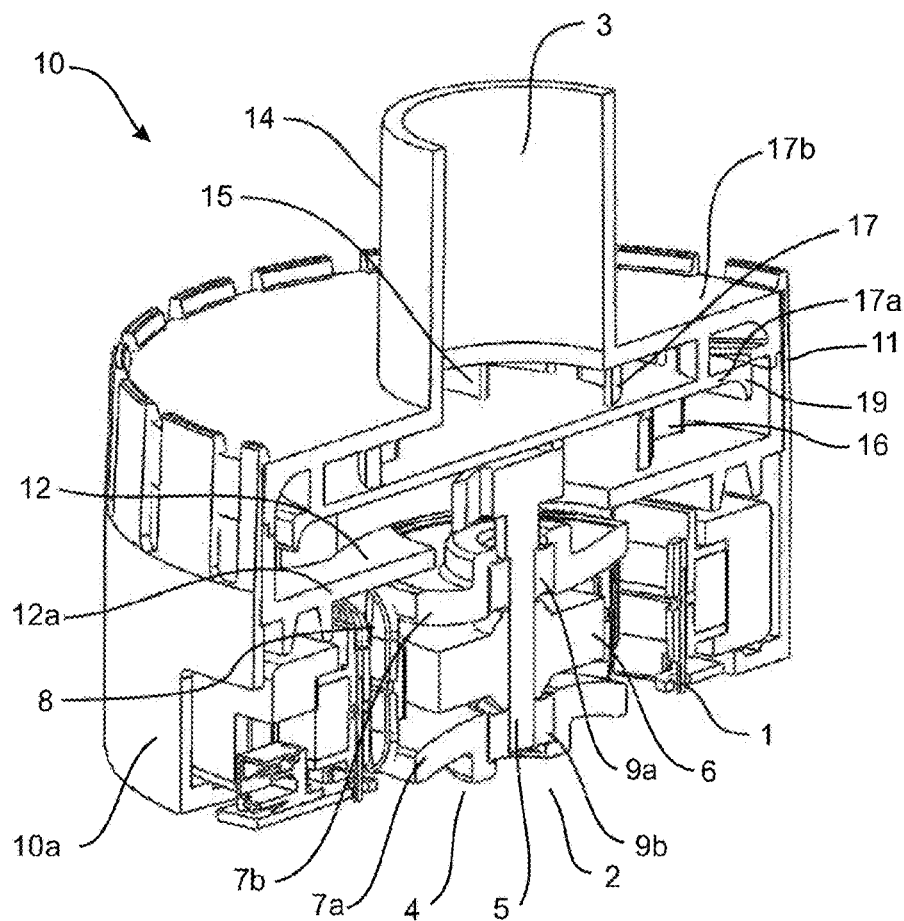
FIG. 1 shows a perspective drawing of a blower for a CPAP apparatus or similar with a diffuser comprising aerofoil diffuser elements according to a first embodiment.

FIG. 1 shows a blower according to the present invention comprising a diffuser with diffuser elements (in the form of protrusions) that reduce noise, produce the required static pressure from dynamic (airflow) pressure and/or mitigate pressure instabilities and/or manages reverse flow so that reverse flow moves in the same direction as forward flow. The diffuser elements take the form of aerofoils, which promote the Coanda effect. The blower can be used in any suitable breathing apparatus such as a continuous positive airway pressure apparatus (CPAP), bi-level apparatus, auto-titration apparatus, high flow therapy apparatus, ventilation apparatus or any other suitable breathing apparatus that would benefit from such a blower. Details of such breathing apparatus, and details of how a blower described herein would be utilised in such a breathing apparatus, will be known to those skilled in the art, and need not be described here. We refer to PCT/NZ2007/00328 published as WO 2008/056993 as an example, which is incorporated herein by reference in its entirety.

The blower 10 of FIG. 1 is an axial inlet/axial outlet blower. It comprises a housing 10a with an axial inlet 2 for ingress of ambient air, and an axial outlet 3 for outlet of (pressurised) air flow to provide to a patient either directly by a suitable conduit and patient interface, or via a humidification apparatus. The blower 10 comprises a motor 4 for driving an impeller 16. The motor 4 could be any suitable motor for driving an impeller 16 in this type of application, such as (but not restricted to) the low inertia motor described in PCT application PCT/NZ2013/000124 published as WO 2013/009193, which is incorporated herein by reference in its entirety. Those skilled in the art will be well versed in the types of motors that could be used, so a full description is not required here, although a brief description will be provided. The motor comprises a stator 1 surrounding a rotor 6. The rotor 6 is coupled to a shaft 5 that is connected to the impeller 16. The shaft 5 rotates on bearings 9a, 9b held in elastomeric mounting discs 7a, 7b. The discs 7a, 7b are coupled to a stator frame 8 coupled to the stator 1 to hold the shaft/rotor assembly in a compliant manner inside the stator 1.

The shaft 5 of the motor 4 extends through an aperture in a shield 12. The shield 12 comprises a flat plate 12a with an annular wall that locates within the housing 10a, and has an annular channel on its underside formed by two protruding walls extending downwards and residing on the stator 1 of the motor 4. The shaft 5 is coupled to an impeller 16, which resides in the housing 10a above the flat plate 12a. The impeller is shown in FIG. 13 by way of example, but can take any suitable configuration such as that shown in PCT/NZ2013/000124 published as WO 2013/009193, for example, which is incorporated herein by reference in its entirety.

A diffuser 17 is positioned in the housing 10a above the impeller 16, and comprises a bottom diffuser plate (diffuser support substrate) 17a and a top diffuser plate (diffuser support substrate) 17b. The top diffuser plate 17b also forms the top of the housing 10a to create an interior volume with the housing 10a and the flat plate 12a. The top diffuser plate 17b has a central aperture 15. An annular tube 14 extends from the central aperture 15, which together form the axial outlet 3. Dynamic airflow generated by the impeller 16 flows up through the diffuser 17 and out through the axial outlet 3.

Figure 2:
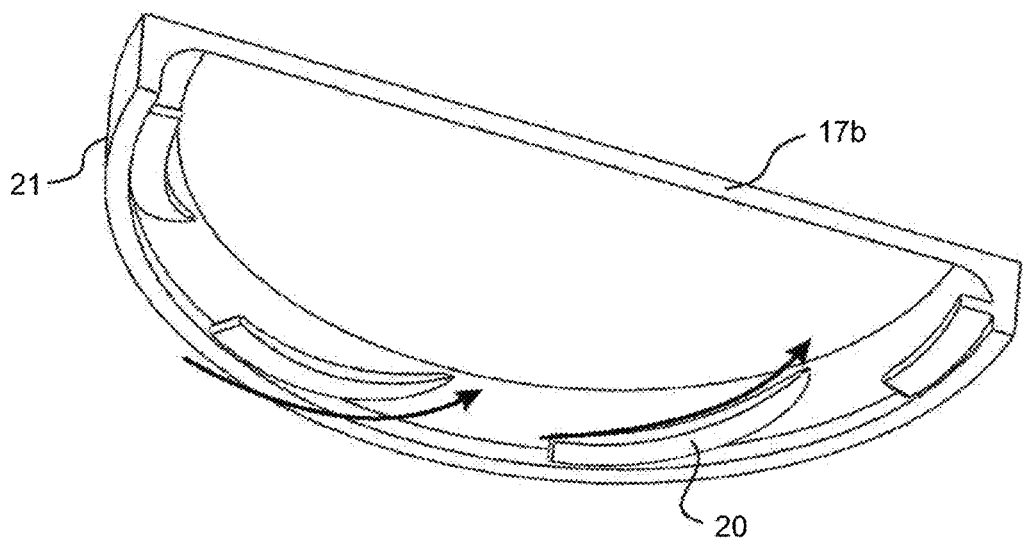
FIG. 2 shows a bottom perspective view of a diffuser plate of the diffuser with diffuser elements.

The diffuser 17 will be described in more detail with respect to FIGS. 2 and 3. With reference to FIG. 2, the top diffuser plate 17b comprises a circumferential/annular wall 21 with circumferential diffuser elements e.g. 20 formed on the internal surface of the wall.

As shown in FIG. 2, each circumferential diffuser element 20 can be in the form of an aerofoil. The aerofoil takes the form of an aerofoil/wing shape/teardrop shape formed as a vane/protrusion. The aerofoil promotes the Coanda effect. Aerofoils can be defined by a NACA number and in the present invention the aerofoils preferably have a NACA number in the 6000-8000 range.

In the preferred embodiment, multiple circumferential diffuser elements 20 are spaced evenly around the internal surface of the annular wall 21, although any suitable number or arrangement could be implemented. In a manner to be described in more detail later, airflow generated by the rotating impeller 16 passes to the circumferential diffuser elements 20, which direct the airflow up to the gap between the top diffuser plate 17b and the bottom diffuser plate 17a. Preferably, the number of circumferential diffuser elements 20 on the annular wall 21 is prime and does not equal the number of impeller blades in order to reduce noise/resonances.

Figure 3A:
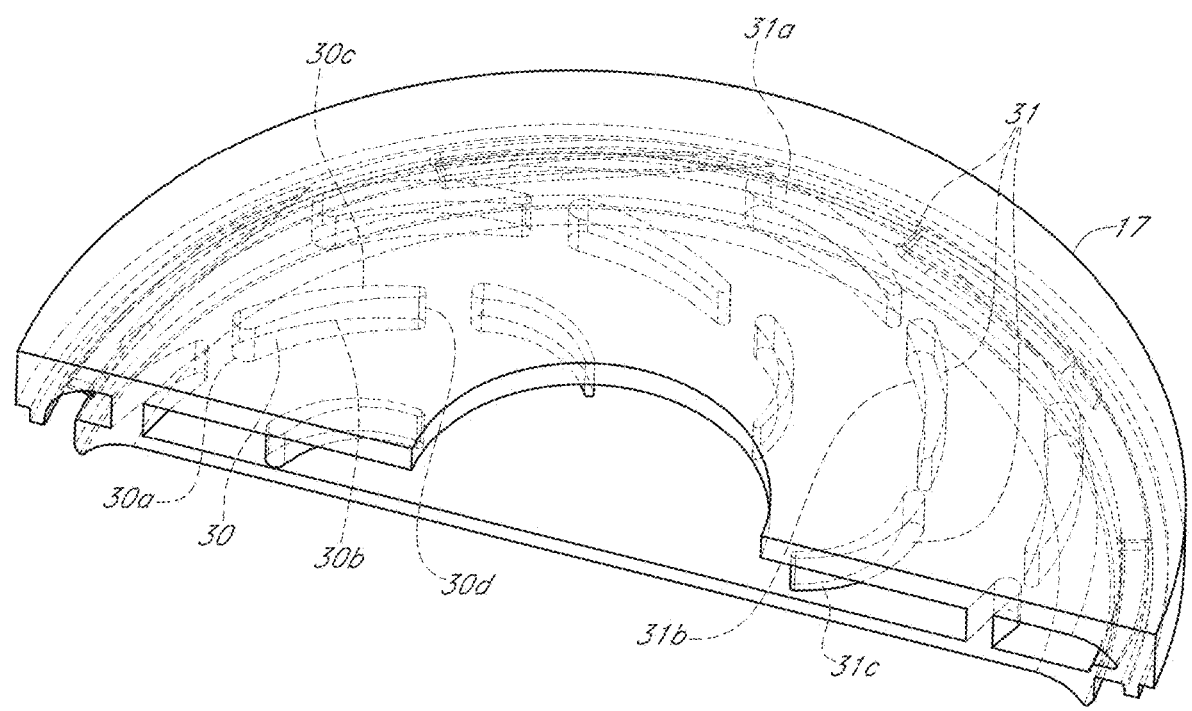
FIGS. 3a, 3b show a top perspective transparent view of the diffuser showing the diffuser elements in a top diffuser plate and diffuser elements between the top and bottom diffuser plates.
Figure 3B:
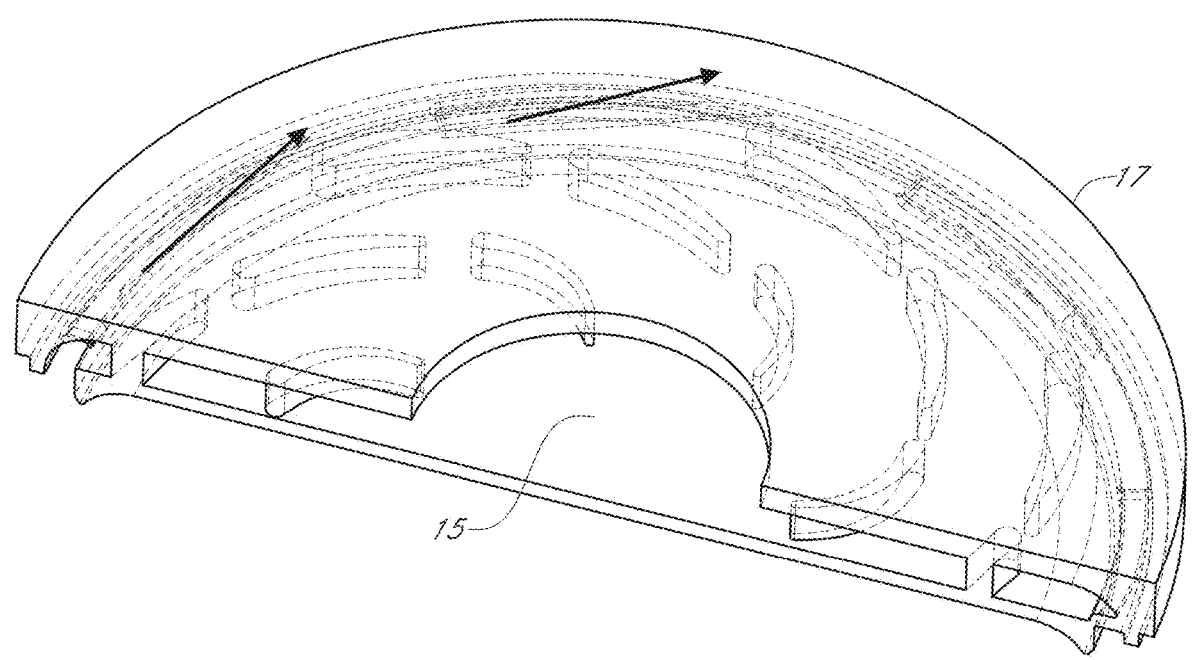

Referring to FIGS. 3a, 3b, the diffuser 17 also comprises further planar diffuser elements e.g. 30 that extend between the bottom diffuser plate 17a and the top diffuser plate 17b. Planar diffuser elements on the top surface of the bottom diffuser plate 17a can be integrally formed with the bottom surface of the top diffuser plate 17b, although this is not essential. The top 17b and bottom 17a diffuser plates may be integrally formed, but that is not essential.

Each planar diffuser element 30 is preferably formed as an aerofoil/wing-shaped/teardrop shaped protrusion/vane promoting a Coanda effect. Again, the aerofoils preferably have a NACA number in the 6000-8000 range. As such, circumferential diffuser elements 20 and planar diffuser elements 30 formed in this manner can be termed "Coanda diffuser elements".

Each planar diffuser element 30 (and optionally each circumferential diffuser element 20) comprises a rounded leading edge, for example 30a, with two opposed curved lateral edges, for example 30b and 30c, one convex and one concave. The two lateral edges, for example 30b and 30c, converge at and join at a curved endpoint, for example 30d, in an elongated tail to create the aerofoil shape.

The planar diffuser elements are arranged into a plurality of cascades. Each circumferential diffuser element 20 on the annular wall 21 has a corresponding/respective series/cascade/succession of planar diffuser elements 31 arranged in a cascading manner. The planar diffuser element e.g. 31a of a cascade 31 has its leading edge proximate the outlet tail of a corresponding circumferential diffuser element 20 on the annular wall 21. As such, the circumferential diffuser element could also (optionally) be considered part of the cascade. The next planar diffuser element e.g. 31b is optionally stepped slightly offset in the X and/or Y direction from the tail of the first planar diffuser element 31a, and each subsequent planar diffuser element e.g. 31c in a cascade is optionally offset in a similar manner from the respective preceding planar diffuser element 31b. The planar diffuser elements 31a-31c of each cascade 31 are arranged and orientated in a manner such that they lie in a curved spiral line 40 (visible in FIG. 4) from the outlet tail of the circumferential diffuser element 20 towards the centre aperture 15 of the top diffuser plate 17b, in a spiral-like arrangement. There is a spacing between ea series of spirally arranged planar diffuser elements 31a-31c and preferably the spacing increases from narrower to wider as the series spirals towards the centre of the diffuser plate 17a.

The bottom diffuser plate 17a also preferably comprises an annular/circumferential wall with a ramped inner surface 19 (also called a "wedge"). This provides a recirculation path for impeller airflow to reduce flutter (it "hides" the blade pass). This works in a manner such as that described in WO2010/126383 filed also by the present applicants.

Figure 4:
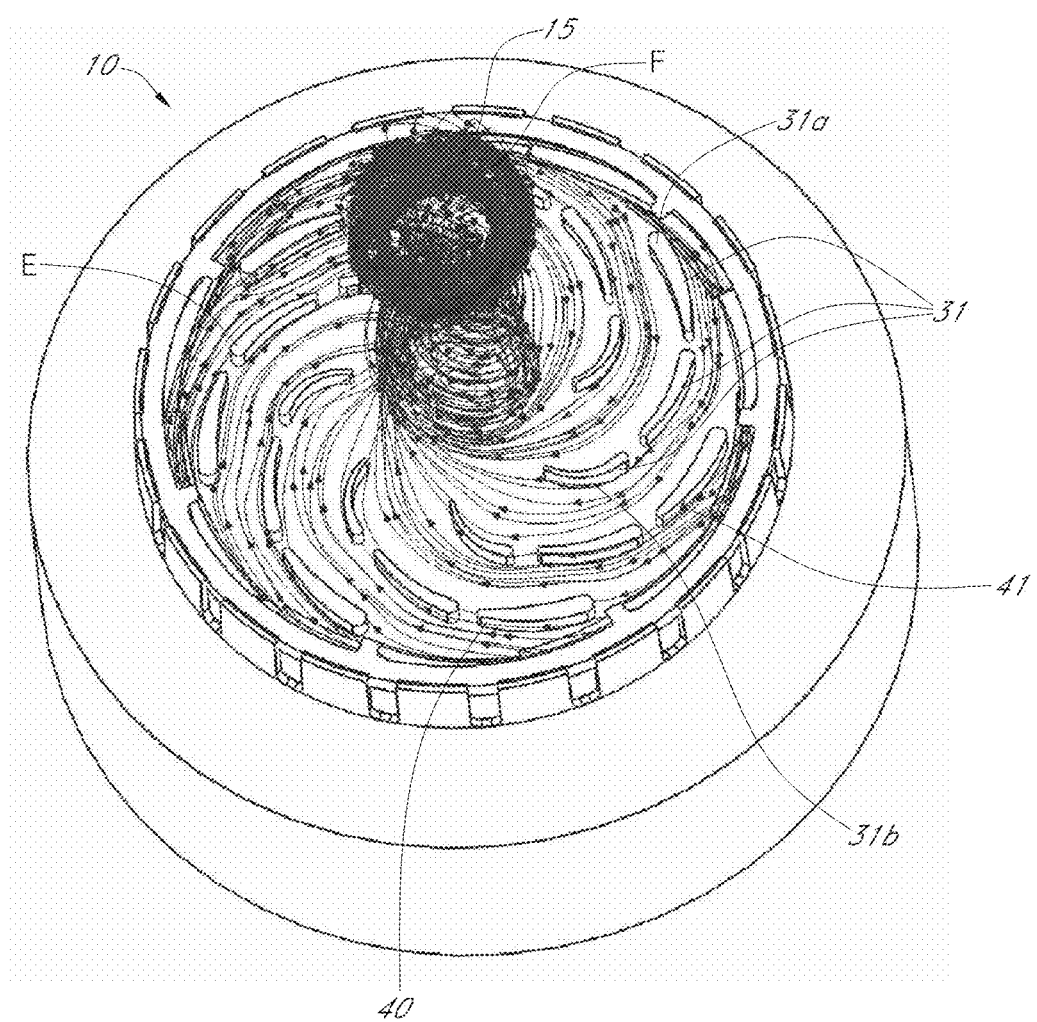
FIG. 4 shows a top perspective view of the blower showing forward airflow from the diffuser elements through an axial outlet.

The operation of the blower 10, and in particular the nature of the air flow in the diffuser 17, will now be described with reference to FIG. 4. As the impeller 16 rotates, airflow is generated at the outer circumference/perimeter of the impeller 16. During forward flow the air is wicked downstream along the gradual sloping aerofoil shape of the circumferential diffuser elements 20 as indicated by the arrows in FIGS. 2 and 3b. Air enters the gap between the diffuser plates 17a/17b from the circumferential diffuser elements 20 with a high tangential velocity as depicted by the lighter coloured flow lines e.g. 41 extending from the circumference of the blower 10 from the circumferential diffuser elements 20 as shown in FIG. 4. The aerofoil shape of the circumferential diffuser elements 20 slightly increases the speed of airflow leaving the 'tail' of the circumferential diffuser element 20, which helps the flow adhere to the planar diffuser elements 31a-31c on the top side of the bottom diffuser plate 17a.

FIG. 4 shows flow lines 41 that demonstrate the (in this case) clockwise movement of the airflow through the cascades e.g. 31 of planar diffuser elements 31a-31c shown on the top side of the bottom diffuser plate 17a (top diffuser plate 17b removed for clarity). The darkness of the line corresponds to flow velocity, with lighter lines corresponding to lower flow velocities and darker lines corresponding to higher flow velocities. The Coanda effect gives the airflow a tendency to "stick" to the outer surface of the aerofoil of a particular planar diffuser element 31a-31c, and the movement along an aerofoil slows down the flow, converting the dynamic pressure of the airflow to static pressure. Additionally, as the airflow moves along the curve e.g. 30b on the front of the aerofoil of a planar diffuser element e.g. 30, the flow gains a little extra velocity (due to Bernoulli's principle) (most visible, for example, at point E FIG. 4) that can be converted to static pressure downstream. The diffused flow then collects in the middle and exits the axial outlet 3 at point F in FIG. 4. The gaps between planar diffuser elements 31a-31c in a cascade 31 help to promote the Coanda effect and to promote the tendency for air flow to "stick" to the cascade 31. As the airflow passes from one diffuser element e.g. 31a to another e.g. 31b in a cascade 31, the airflow "re-engages" with the diffuser element, thus promoting airflow to remain closer to the cascade 31 of diffuser elements along the entire length. The illustrated diffuser 17 contrasts with a single continuous spiral diffuser, from which airflow will "detach" from the diffuser much earlier.

Figure 5:
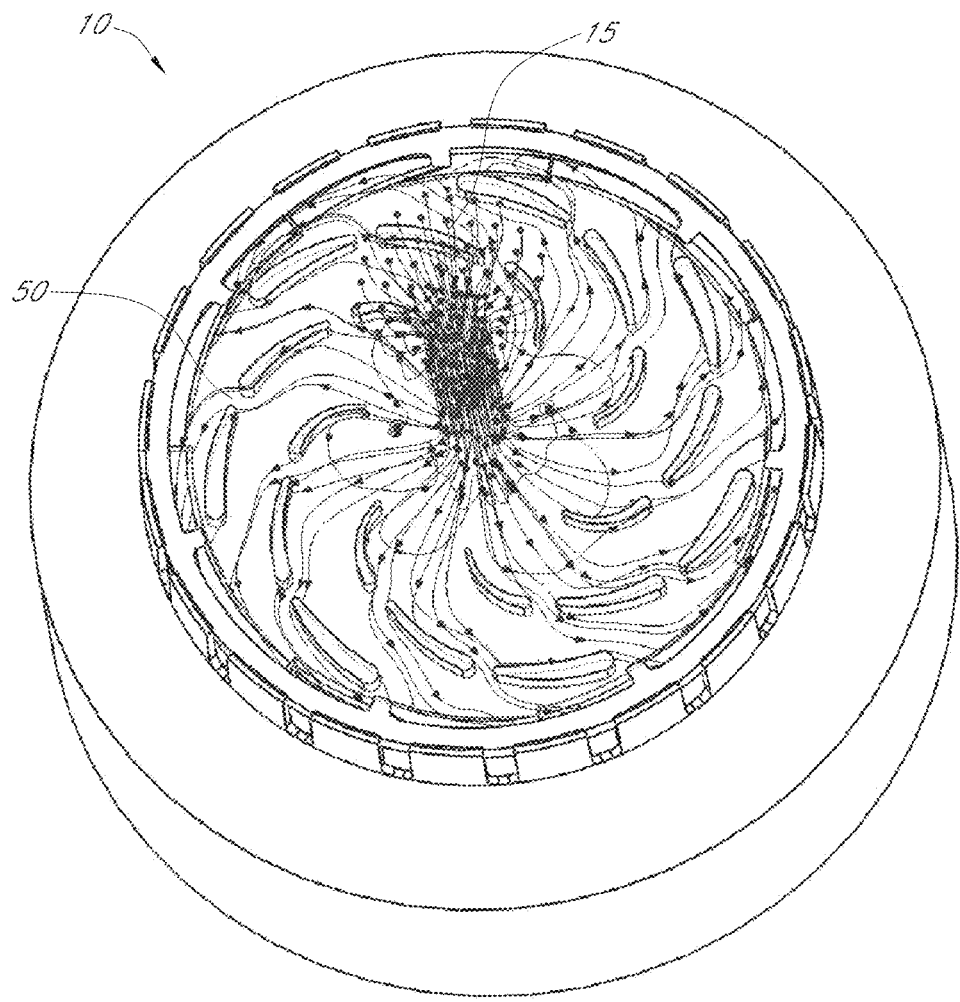
FIG. 5 shows a top perspective view of the blower showing reverse airflow along the diffuser elements.
Figure 6A:
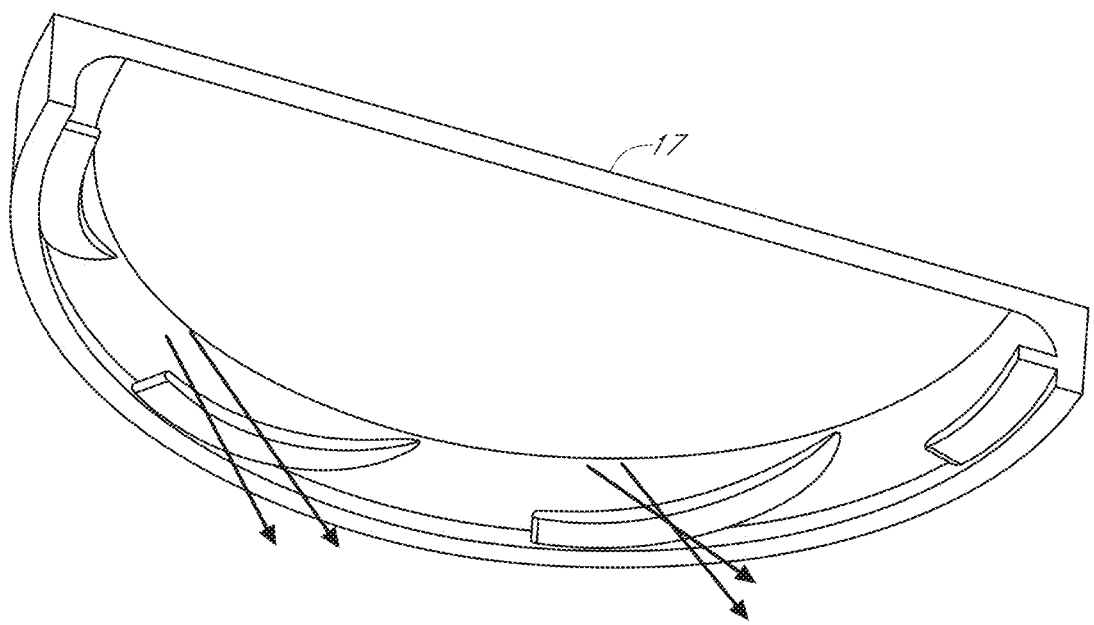
FIG. 6a shows reverse airflow on a bottom perspective view of the top diffuser plate with diffuser elements.
Figure 6B:
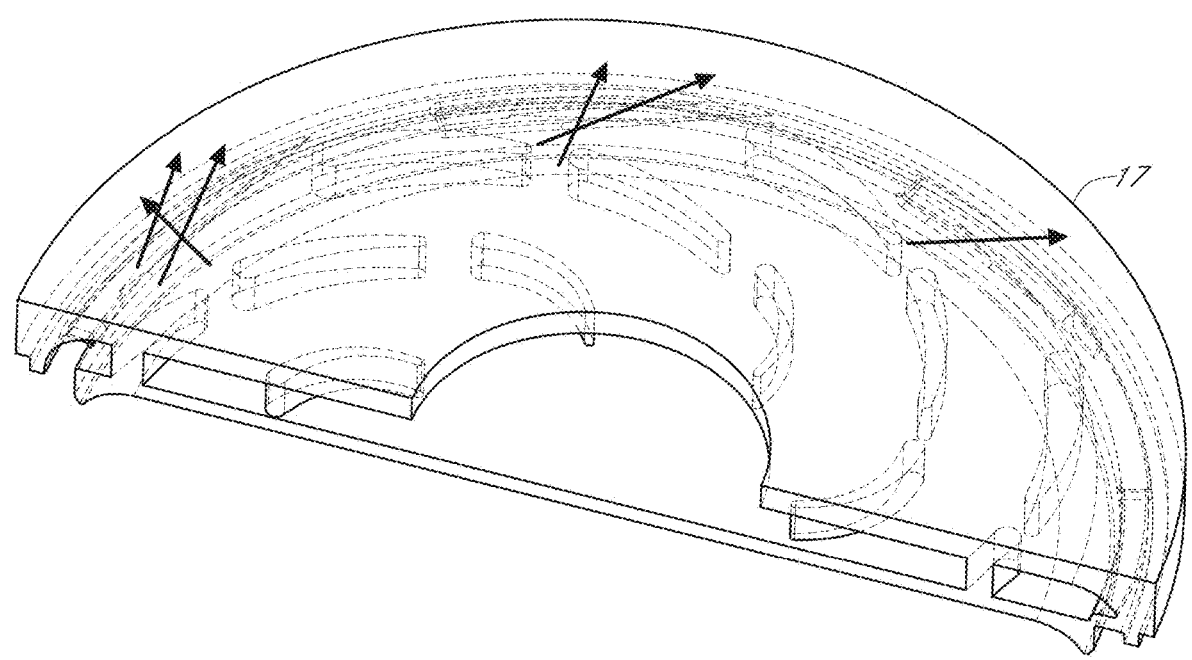
FIG. 6b shows reverse airflow on a bottom perspective transparent view of the diffuser showing the diffuser elements.

FIG. 5 shows flow lines e.g. 50 that demonstrate the movement of reverse airflow from the patient through the aerofoil diffuser element cascade in the blower 10. The diffuser configuration handles reverse flow also. As gases enter the blower from the axial outlet 3, they curve around the aerofoils in such a way that towards the perimeter of the blower 10, they can re-enter the forward stream—not opposed to the rotary motion of the impeller 16, but instead aligned with or at least not moving against the direction of the rotary motion of the impeller 16. This effect is promoted by the gaps between each circumferential diffuser elements 20 and planar diffuser element 31a-31c in a cascade of elements 31 to provide alternative paths for reverse flow. FIGS. 6a and 6b show light (FIG. 6a) and dark (FIG. 6b) arrows similar to those shown in FIG. 3a and FIG. 3b, except indicating possible motion of flow lines under reverse flow. As can be seen, the flow lines of FIGS. 5 to 6b move roughly in the same tangential direction relative to the impeller 16 as in FIG. 2. This redirection of air flow using the aerofoils significantly reduces audible noise resulting in shearing upon exhalation into the blower assembly.

Therefore, the combination of diffuser elements arranged in cascade spirals improves static pressure and provides a path for reverse flow.

While preferably the diffuser elements 20, 30 are aerofoil shaped, this is not essential. The aerofoil shaped diffuser elements 20, 30 described in this embodiment are preferable, although not essential. The diffuser elements 20, 30 could simply be used without the aerofoil shape. The use of circumferential diffuser elements 20 in the present invention reduces blade pass noise. The pulsating and unsteady flow stream created by traditional diffuser vanes is softened by the distance that these diffuser elements 20 are placed away from the blade tips (proximity reduced).

A wedge 19 also helps in reducing blade tip disturbance in a manner described above and the aerofoils may take a portion of the velocity in the annular vortex (phantom impeller) leaving enough velocity there to maintain a stable source of spinning fluid (gas) to draw from.

Referring to the single stage and multistage blower described below, the gradual negative 'rake' or introduction ('scoop') to the top layer provided by the aerofoils is in contrast to other scoops used in centrifugal compressors in that the gradual aerofoil scoop is more efficient and less disruptive to the main flow stream—thus this scoop creates less blade pass tonal noise than those other scoops. Additionally the aerofoil shape of the recession/'tongue' slightly increases the speed of flow leaving the 'tail' of the recession, which helps the flow adhere to the Coanda effect on the top side of the diffuser plate as described in the next two paragraphs.

The teardrop aerofoil diffuser elements are cascading and are slightly stepped out of place with one another. As the air moves from the Coanda recess onto the plate, the air may still have a tendency to stick to the inside of the aerofoil, but then the air moves across the aerofoil and collects additional velocity when moving off the 'head' of the next aerofoil (which it strikes because of the stepped nature of the aerofoils)—the additional velocity makes the air more likely to follow to the Coanda effect and ride along the outside of the aerofoil. The cascading aerofoils give the air several chances to change sides, and because of this a more even distribution/diffusion of roughly laminar flow lines occurs both along the aerofoils and in between the cascades of aerofoils.

In the illustrated FIG. 1, flow moving along the planar diffuser elements 30 from the ends of the circumferential diffuser elements 20 to the central aperture 15 is redirected such that at least a portion of the substantially tangential movement of the flow induced by the impeller 16 is translated into substantially axial movement through the annular tube 14. When changing direction in this space, flow vortices may be generated that consume additional mechanical energy ('shock loss') and increase the resistance to flow of the gas passageway defined between the bottom diffuser plate 17a and the axial outlet 3. Decreasing the amount of mechanical energy and resistance to flow will minimize pressure loss and decrease the generation of heat and/or noise caused by such vortices.

Figure 7A:
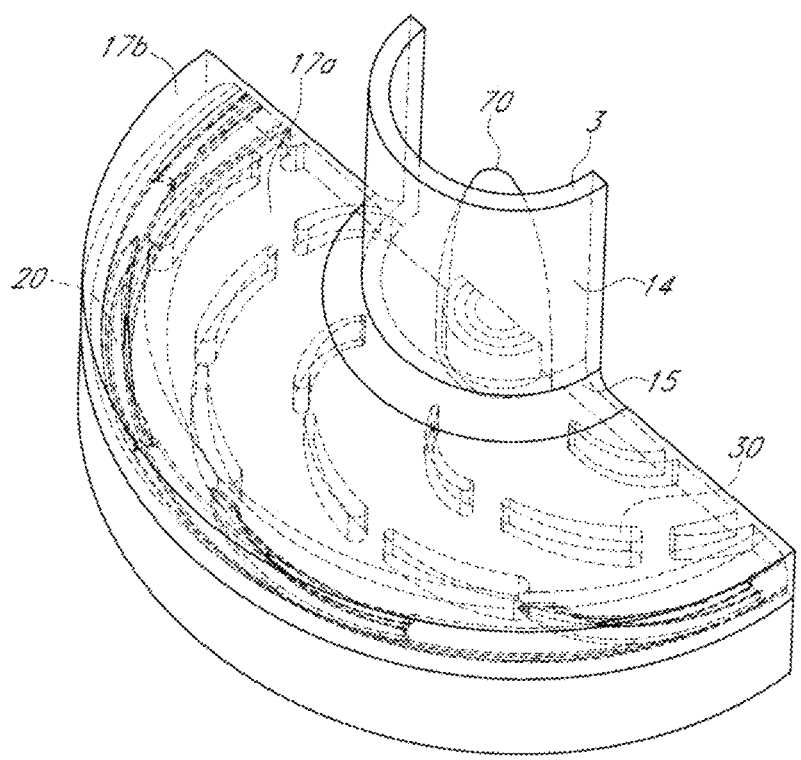
FIGS. 7a, 7b show partial perspective and cross-section views of the diffuser with a flow guide.
Figure 7B:
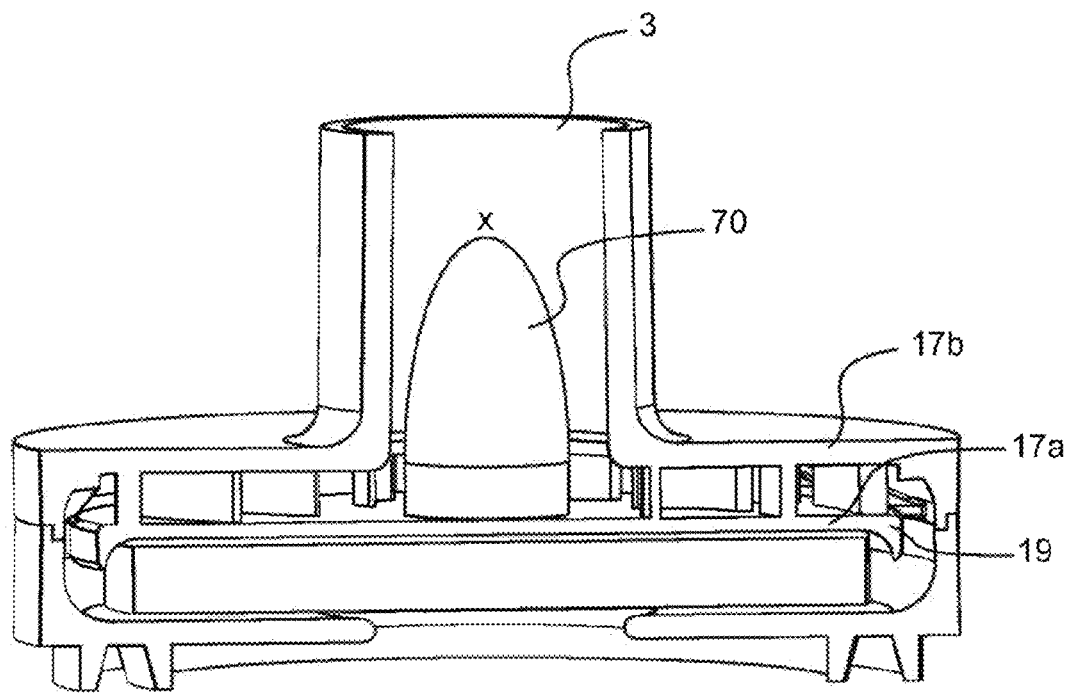

In some configurations, and as illustrated in FIGS. 7a, 7b, a flow guide 70 can be placed on the bottom diffuser plate 17a. The flow guide 70 promotes a relatively smooth redirection of flow from the diffuser 17 such that shock loss is reduced. As shown in FIGS. 7a, 7b, the flow guide 70 comprises an annular structure beginning at the bottom diffuser plate 17a. The flow guide 70 is co-axial with the central aperture 15. The annular structure extends towards the annular tube 14 and tapers in diameter towards a point x. The taper of the flow guide 70 increases in severity along the length of the flow guide 70, imparting to the flow guide 70 a 'bullet' or 'torpedo' shape. In the shown configuration, the flow guide 70 is integrally formed or in the form of a single continuous part together with the bottom diffuser plate 17a.

In some configurations, the flow guide 70 may be horizontally offset from the central aperture 15. In some configurations, the taper of the flow guide 70 may be constant along the length of the flow guide 70. In some configurations, the average taper of the flow guide 70 along the length of the flow guide 70 may be 6 or about 6 degrees. In some configurations, the flow guide 70 may be a separate component from the bottom diffuser plate 17a. The flow guide 70 may be joined with the bottom diffuser plate 17a using other means, including but not limited to the use of adhesives or welding (e.g. high frequency or ultrasonic welding). In some configurations, the flow guide 70 may be attached to the bottom diffuser plate 17a, top diffuser plate 17b, and/or annular tube 14. In some configurations, the flow guide 70 may comprise other shapes, including but not limited to columnar, cylindrical, conical, frustoconical or pyramidal shapes.

Additionally, in some configurations, sections of the top diffuser plate 17b defining the central aperture 15 may be bevelled or arcuate instead of flat or sharp. Smoothing the introduction to the central aperture 15 can discourage the formation of flow vortices that lead to shock loss.

It is not necessary for the blower/diffuser to have both circumferential elements and planar diffuser elements. In one possible embodiment, the blower/diffuser will only have circumferential diffuser elements. In another possible embodiment, the blower diffuser will only have planar diffuser elements.

Figure 8:
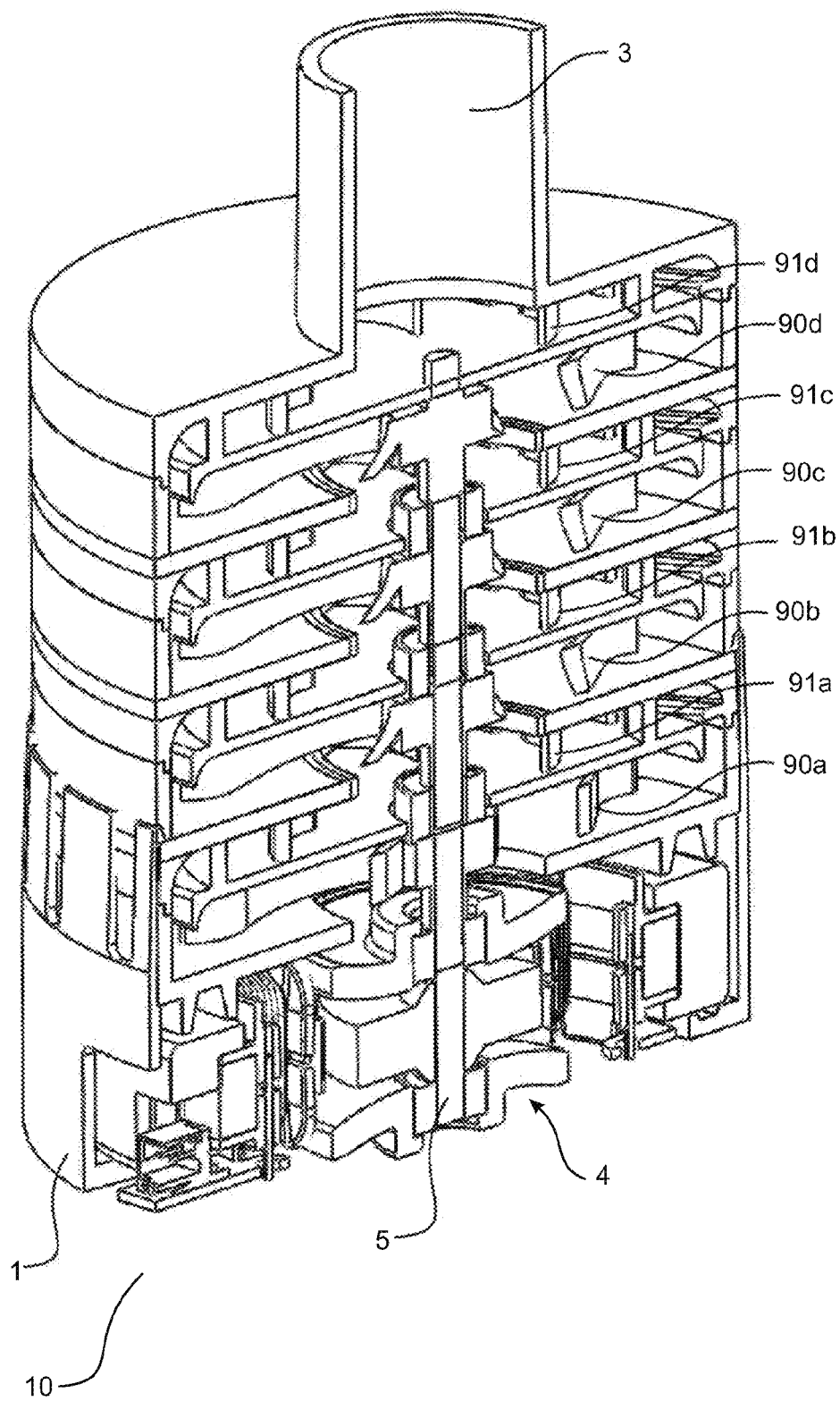
FIG. 8 shows a perspective drawing of a multistage blower for a CPAP apparatus or similar with multiple diffusers with diffuser elements.

The diffuser 17 described in the first embodiment can be utilised in a multistage blower, such as that shown in FIG. 8. Some means of diffusion is required between stages and a multistage blower can be used to convert as much dynamic pressure as possible to static pressure so that successive impellers can impart as much additional dynamic pressure as possible. Generally, a multi-stage blower system is capable of much quieter operation than a single-stage blower system, and particularly for a wearable CPAP apparatus, the mitigation of stalling sounds during reverse flow is highly desired because the blower would be much closer to the face than it would be in a non-wearable CPAP system.

The multistage blower shown in FIG. 8 has the same elements as shown in FIG. 1, except that there are multiple impellers and diffusers in series (each stage comprising an impeller and diffuser), with the impeller of each stage coupled to the output shaft of the motor. The diffuser and impeller of each stage have the same configuration as described with reference to FIG. 1. In FIG. 8, a series of four diffuser/impeller stages are shown, but any suitable number of stages could be provided. As shown, a motor output shaft 5 extends through the housing 10a of the blower 10. A motor 4 is provided at the bottom of the blower 10, as previously described in relation to FIG. 1. Stage I comprises an impeller 90a and first diffuser 91a. Airflow passing through the first diffuser 91a exits axially through the top diffuser plate into the bottom plate of the next stage where the impeller 90b of stage II imparts further energy/velocity into the airflow. The airflow passes through the aerofoils of the stage II diffuser 91b into the diffuser element cascades 31 of the stage II diffuser 91b and then out into the impeller 90c of stage III and through the stage III diffuser 91c. This continues through all the stages until the final stage is reached and the diffused air from that stage is passed through the axial outlet 3.

Axial Inlet, Radial Outlet Embodiment

Figure 9A:
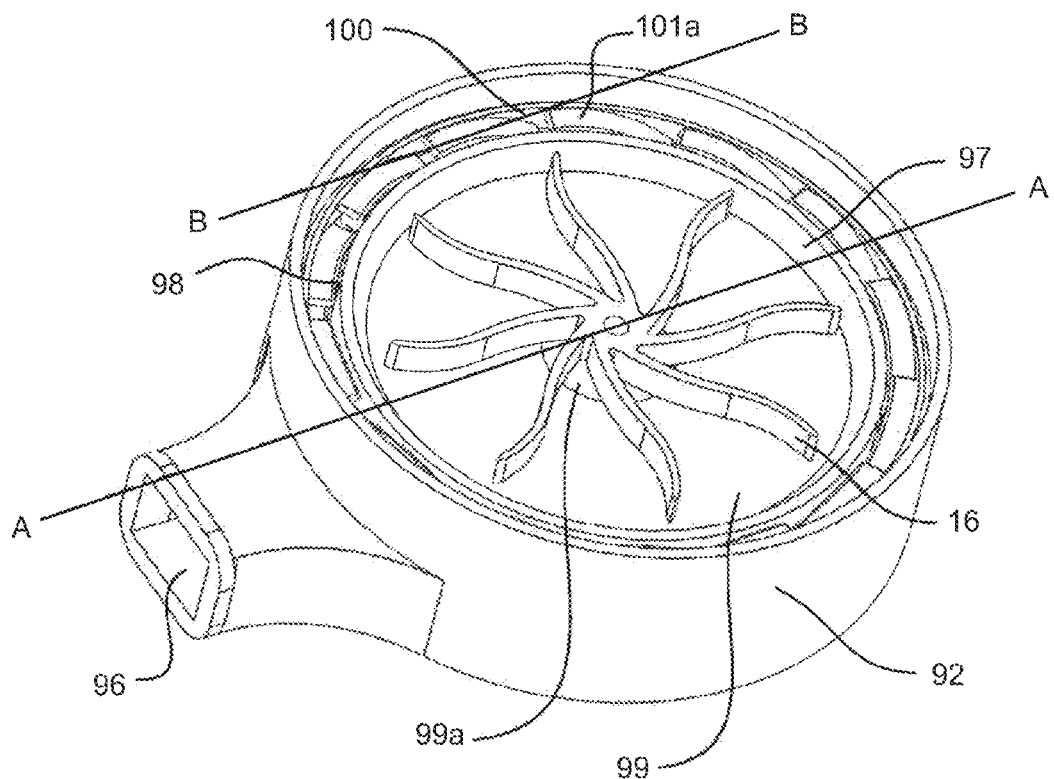
FIGS. 9a, 9b, 9c show perspective drawings of a blower for a CPAP apparatus or similar with a diffuser comprising diffuser elements in a ring according to a second embodiment
Figure 9B:
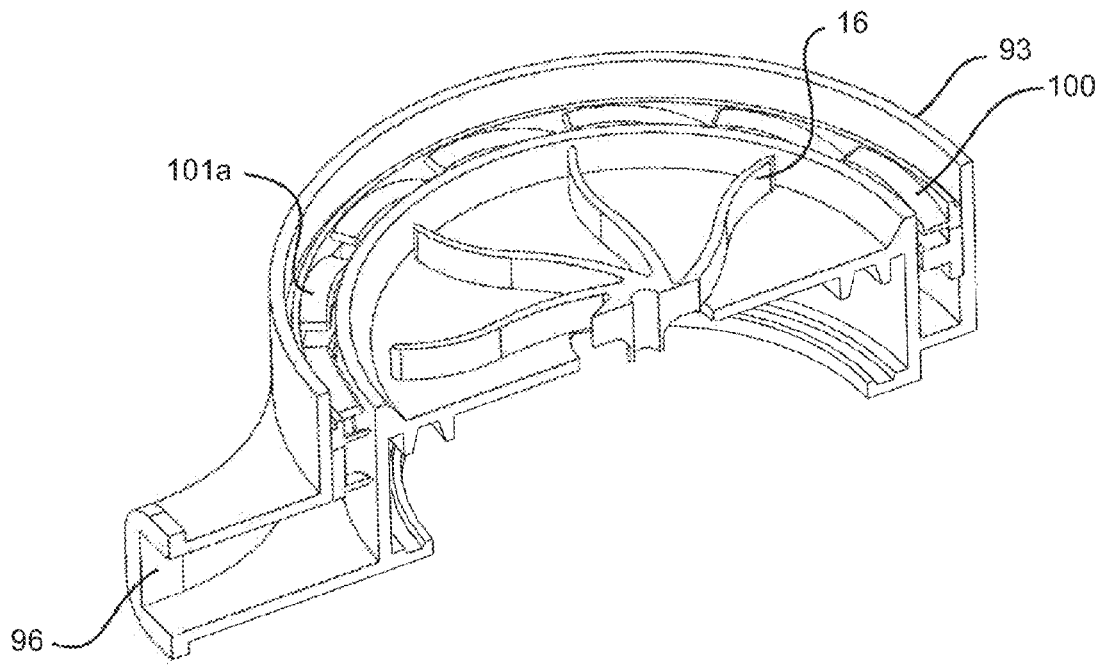
Figure 9C:
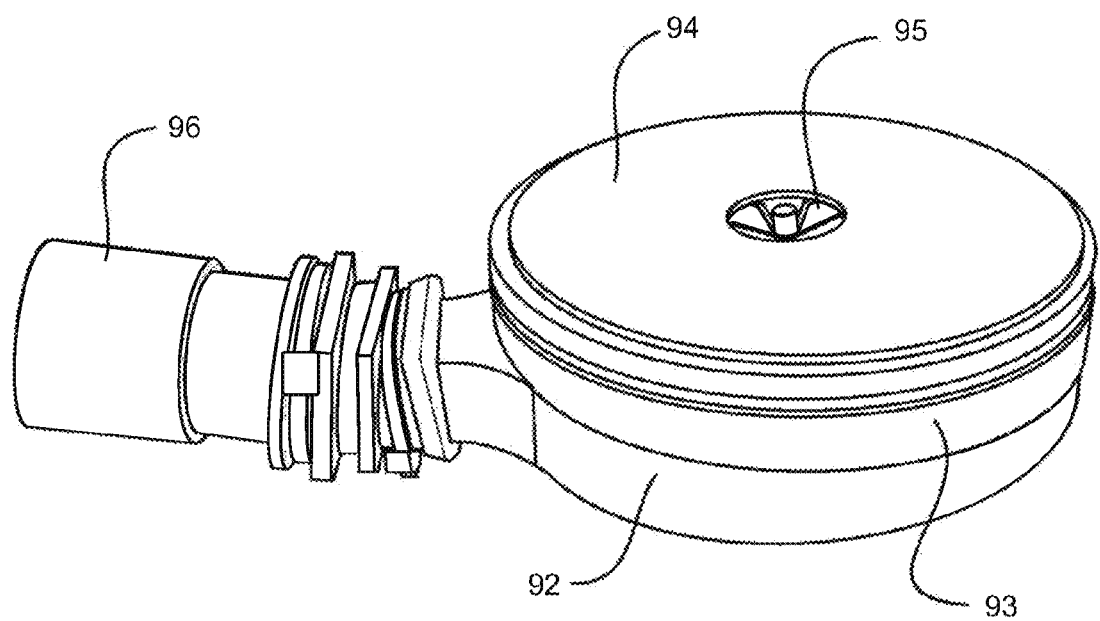
Figure 10A:
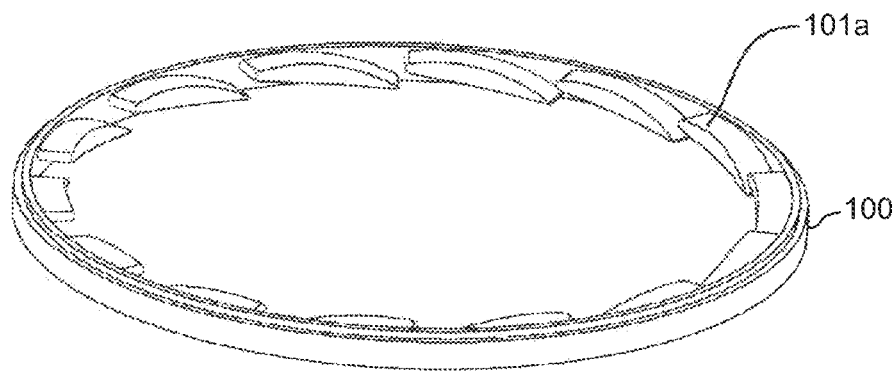
FIGS. 10a-10c show a diffuser comprising diffuser elements in a ring in further detail.

In an alternative embodiment, the blower could be in an axial inlet-radial outlet configuration. Referring to FIGS. 9a, 9b and 9c, the blower 92 comprises a housing 93 including a top plate 94 forming an interior region within the housing. The top plate 94 has a central aperture 95 for axial air input, and an outlet 96 radially extending from the housing. Preferably, the outlet 96 is a symmetrical radial outlet. Namely, the outlet extends radially out along a line "A"

extending from the centre of the blower through the perimeter/housing of the blower. This contrasts to a more tangential type outlet which extends from the housing but along a line "B" offset from a centre line extending from the centre of the blower through the perimeter/housing. An annular wall 97 within the housing creates an annular volute 98, from which the radial outlet extends, and a plate 99 with a central aperture 99a is provided for creating an impeller region within the housing and separating the motor from the impeller. The motor shaft extends through the aperture and connects to an impeller that sits in the impeller region. A diffuser ring (annular diffuser support substrate) 100 with diffusion elements e.g. 101a, 101b is situated within the volute 98 within the housing 93. The diffusion ring 100 can be seen in FIGS. 10a-10c. The diffusion ring 100 comprises (circumferential/ring) diffusion elements e.g. 101a, 101b on the interior surface, the elements/vanes being preferably aerofoil shaped, such as described in the previous embodiment. Several diffuser rings 100 can be stacked vertically 101 within the volute 98. Preferably the diffuser rings 100 are slightly offset (in a similar manner to the planar diffuser elements as described in the previous embodiment) from one another with respect to the elements 101a, 101b to create a sequence of cascading diffuser elements 101 such that moving in an axial direction where each cascade comprises offset elements that spiral in a helical manner around the circumference of the impeller on the inner surface of the rings.

Figure 10B:
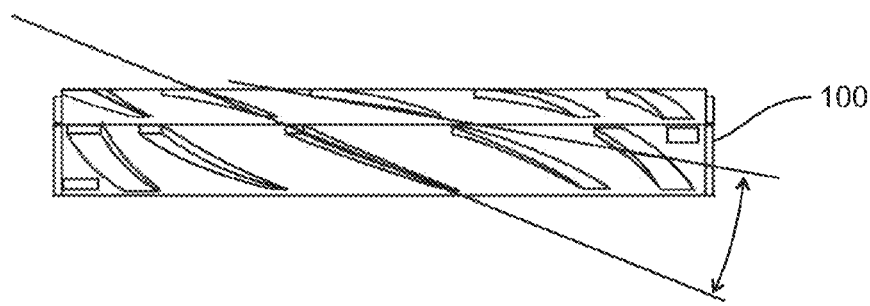
Figure 10C:
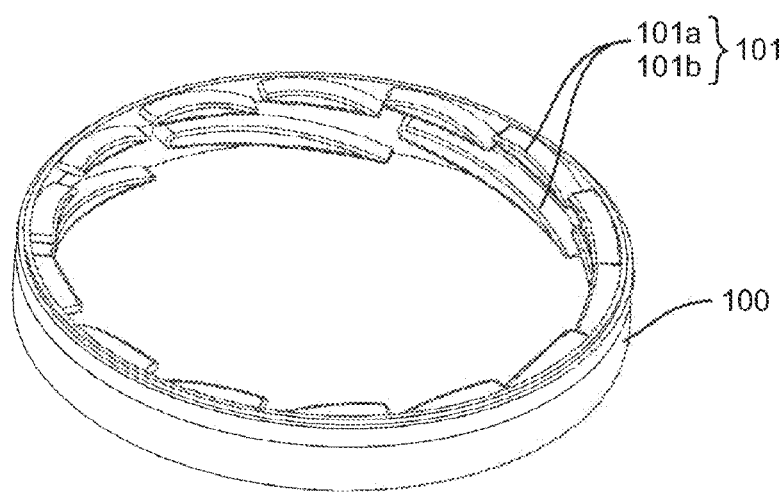

In another embodiment they are not separate rings, but rather a single elongated cylinder (which can still be termed a "ring" or annular support substrate) with an inner surface for the elements. This is similar to the arrangement in the first embodiment, but rather than the cascade of diffuser elements 101 being arranged on a flat plate 17a in a horizontal plane, the ring/circumferential diffuser elements can be arranged vertically/axially on the interior of an annular surface created from the inner surface of the stacked diffuser rings 100. The angle between the offset ring diffusion elements 101a, 101b in the stack is preferably around 12° as shown in FIG. 10b.

During operation the motor rotates the impeller, and the impeller generates an air flow at its perimeter. The high velocity air flow at the parameter is pulled by the Coanda effect to the diffusion elements 101a, 101b on the rings and diffused in a similar manner to that explained in relation to the first embodiment, except only that the flow is diffused axially rather than radially. The axial diffusion creates static pressure and the airflow passes through the radial outlet.

Figure 11A:
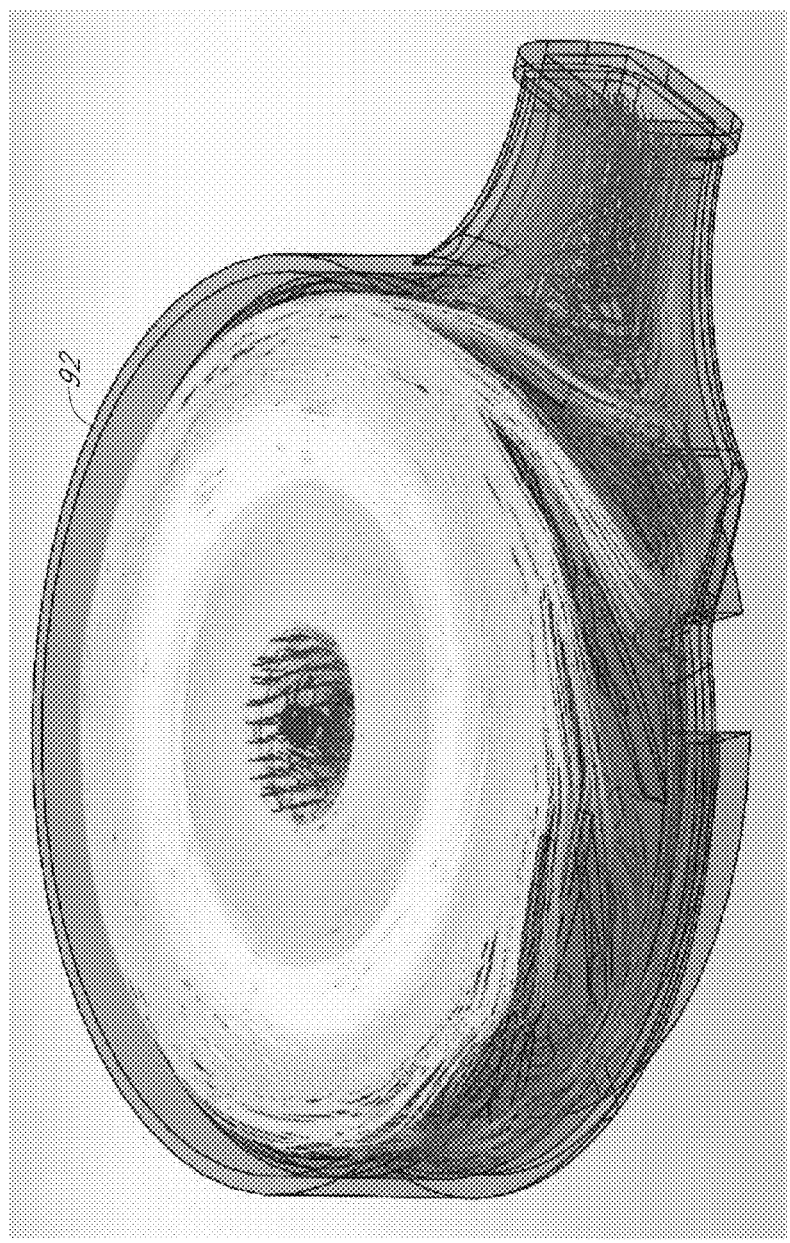
FIGS. 11a-11e show the forward and reverse airflow in the second embodiment.
Figure 11B:
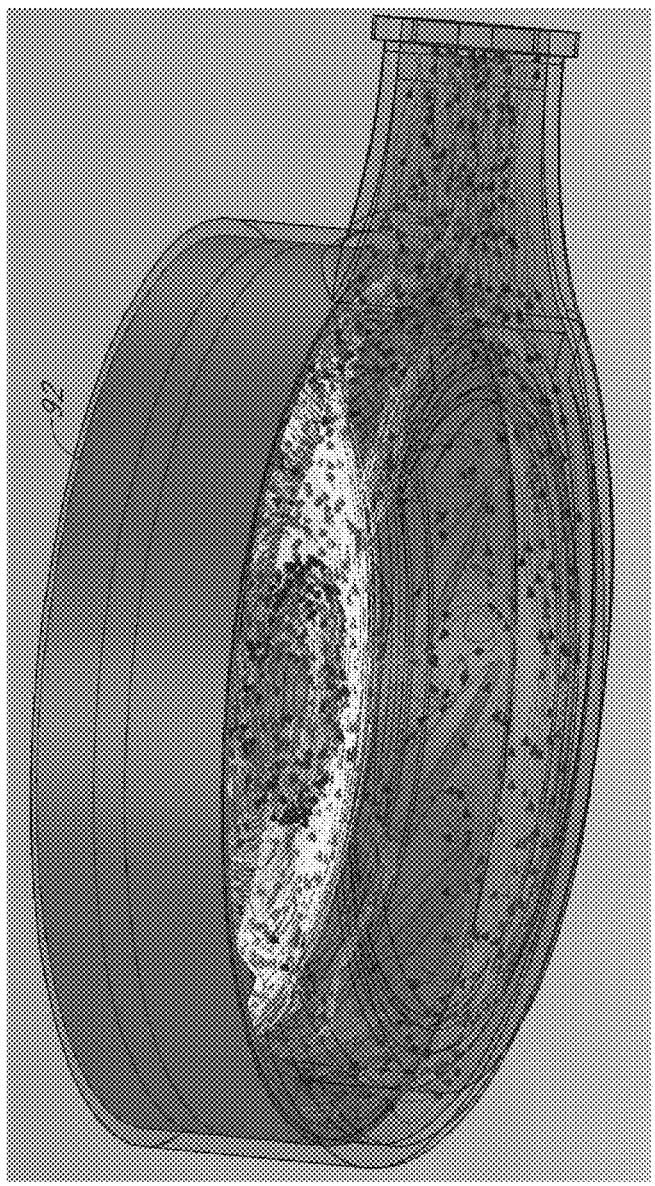
Figure 11C:
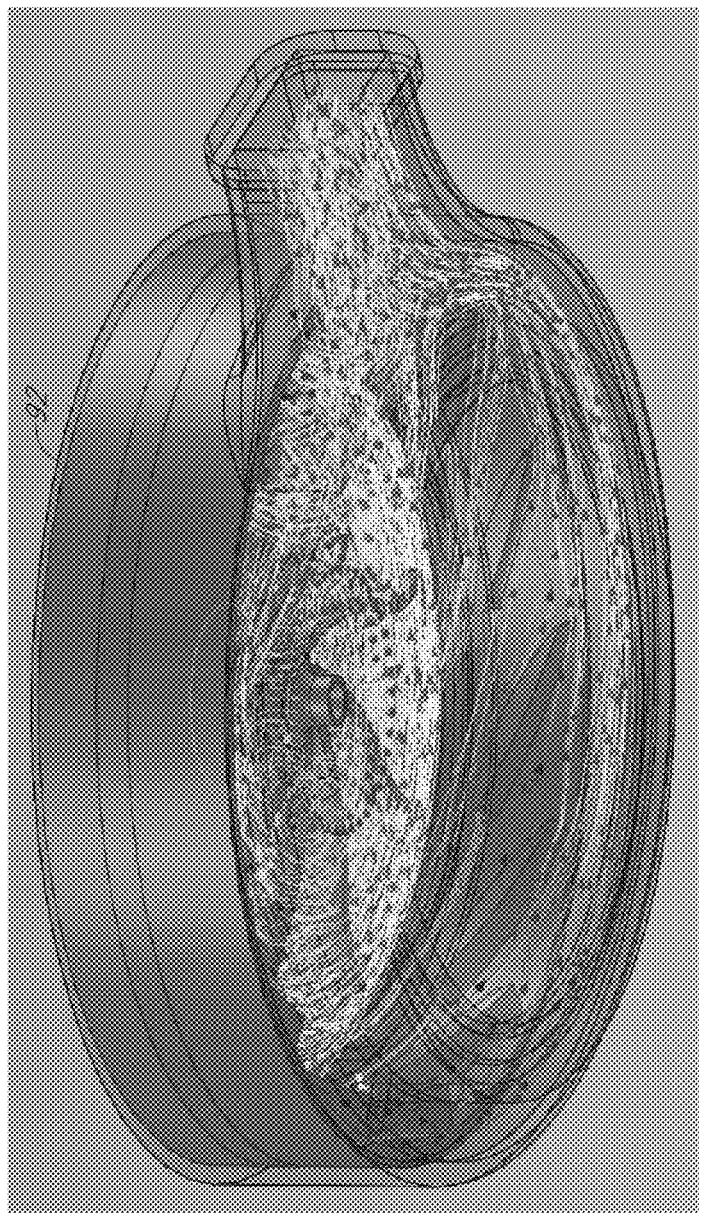
Figure 11D:
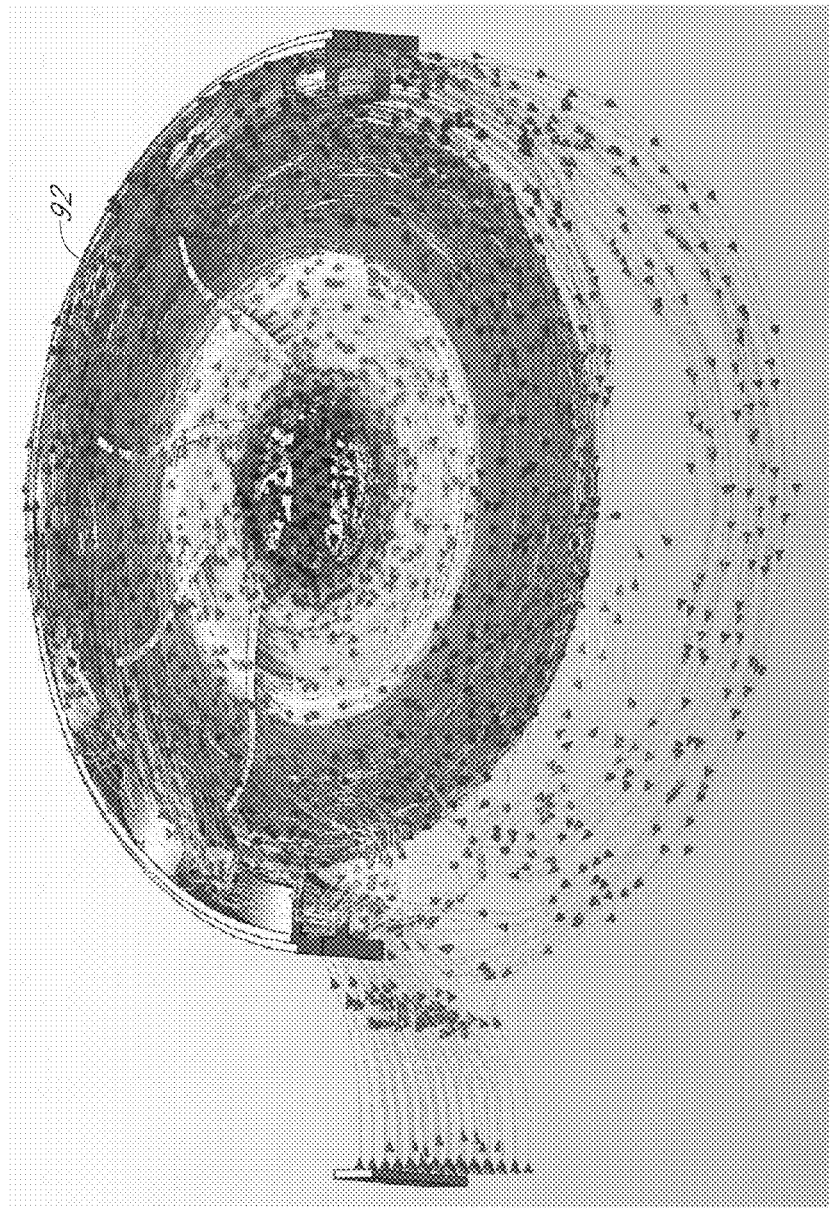
Figure 11E:
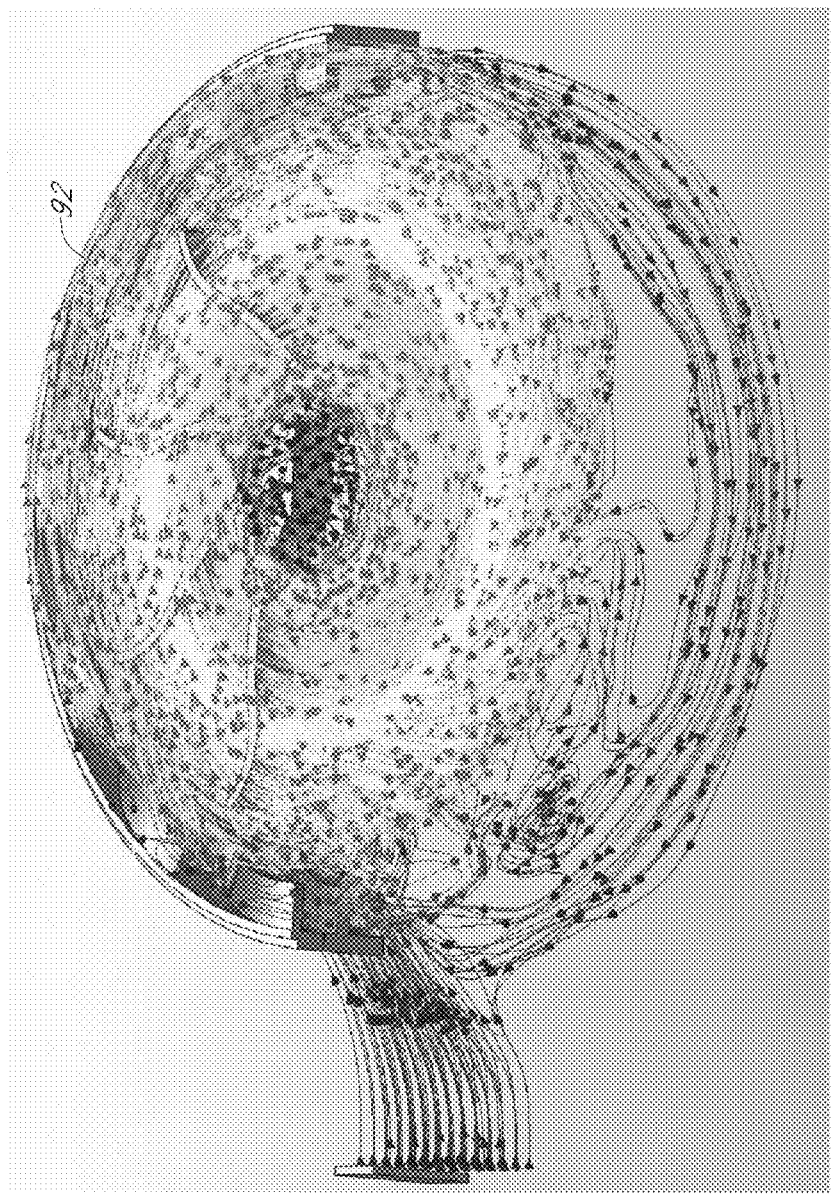
Figure 12:
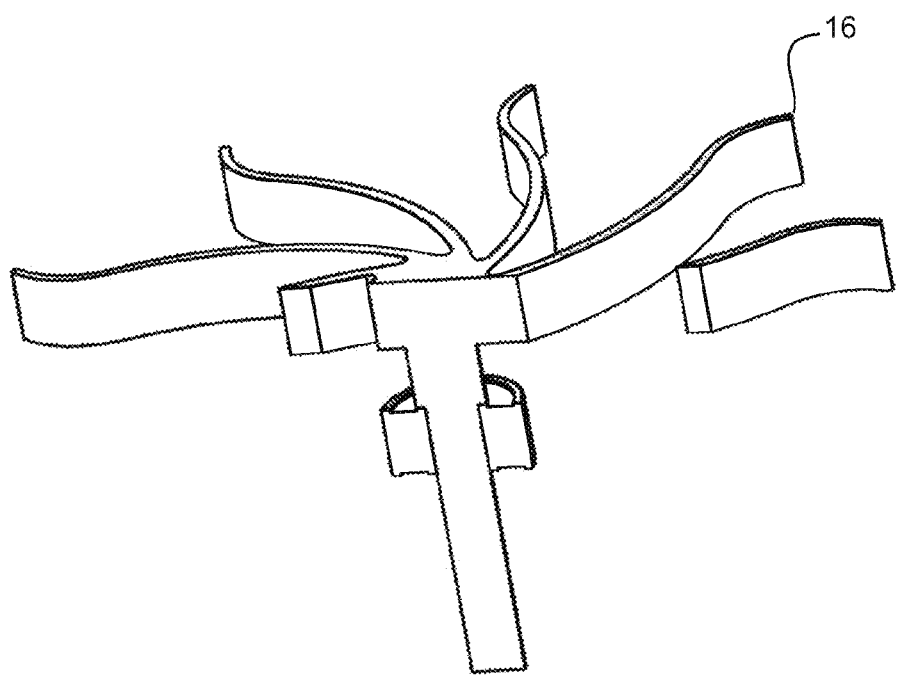
FIG. 12 shows a possible impeller.

FIGS. 11a, 11b, 11c show forward airflow, with lighter colour showing high velocity air flow, and darker colour showing lower velocity air flow. As can be seen, high velocity dynamic airflow pressure at the inlet is converted to low velocity static airflow pressure at the outlet by way of the diffuser. FIGS. 11d, 11e show reverse flow.

Alternative Embodiments

The embodiments described are not exhaustive of the possible configurations that a blower according to the invention could take. Cascading (preferably) aerofoil diffuser elements of a given size (on the top of the diffuser plate and/or a diffuser ring arrangement) could take other possible sizes, shapes, or configurations. Having a (preferably) aerofoil diffuser element that is too short, or having too many diffuser elements will reduce the continuity necessary for the Coanda effect to be exhibited, while having an diffuser element that is too long will allow the boundary layer to stagnate to the effect that the Coanda effect will not be seen. Also enough space is required between the diffuser elements to accommodate the movement of reverse flow in order to bring about the redirection effect depicted. While an axial inlet/axial outlet blower could be used with a wearable CPAP device, this is not preferable as it is awkward. An axial inlet-radial outlet (relative to the impeller) blower as described in the second embodiment would be preferred. The feature of the above blower system is separated diffusion elements that can be cascaded, which can be readily implemented in an axial-radial blower system, as described above.

The cascading diffuser element configuration could be used in nearly any blower type, including but not limited to axial-inlet axial-outlet, axial-inlet radial-outlet, axial-inlet tangential outlet, radial-inlet radial-outlet, radial-inlet tangential-outlet, tangential-inlet tangential outlet, etc. The teardrop configuration initially discussed dealt with an axial-inlet axial-outlet type blower with diffusion happening when flow moved over the teardrop plate outwardly to inwardly. Many directions of diffusion are possible as long as the cascading diffusion elements are used.

What is claimed is:

1. A blower for a breathing apparatus comprising:
a housing with an inlet and an outlet,
a motor within the housing for rotating an impeller,
a diffuser within the housing between the impeller and the outlet, the diffuser comprising a plate with diffuser vanes, the plate including a flow guide extending from the plate and tapering in diameter towards a point, the flow guide being arranged to promote a smooth redirection of flow from the diffuser towards the outlet, and
the diffuser vanes being arranged in a plurality of cascades on the plate, each cascade comprising a series of diffuser vanes configured to accommodate movement of reverse airflow,
wherein a spacing between each pair of adjacent cascades of the plurality of cascades increases from narrower to wider as the each pair of adjacent cascades extend toward a center of the plate, wherein the spacing between the each pair of adjacent cascades is defined in a direction normal to a centerline extending between the pair of adjacent cascades.

2. The blower according to claim 1, wherein each diffuser vane is offset from adjacent diffuser vanes in each cascade.

3. The blower according to claim 1, wherein the diffuser vanes in each cascade are arranged along a curved spiral line from a perimeter to the center of the plate.

4. The blower according to claim 1, wherein each diffuser vane includes a rounded leading edge and two opposed curved lateral edges.

5. The blower according to claim 4, wherein the two opposed curved lateral edges converge at and join at a curved endpoint, in an elongated tail.

6. The blower according to claim 4, wherein the diffuser vanes are aerofoils.

7. The blower according to claim 1, further comprising a plurality of circumferential diffuser elements arranged proximate a perimeter of the plate to direct airflow from the perimeter of the impeller to the diffuser vanes.

8. The blower according to claim 7, wherein the diffuser vanes cascade in a spiral from a corresponding circumferential diffuser element of the plurality of circumferential diffuser elements towards the center of the plate.

9. The blower according to claim 7, wherein at least one diffuser vane in each cascade of the plurality of cascades is entirely inward of the plurality of circumferential diffuser elements.

10. The blower according to claim 7, wherein at least one diffuser vane in each cascade of the plurality of cascades has a leading edge that is closer to the center of the plate than an outlet tail of each circumferential diffuser element of the plurality of circumferential diffuser elements.

11. The blower according to claim 1, wherein the taper of the flow guide increases along a length of the flow guide.

12. The blower according to claim 1, wherein the outlet includes an annular tube and a central aperture.

13. The blower according to claim 12, wherein the outlet is beveled or arcuate where the outlet defines the central aperture.

14. The blower according to claim 1, wherein the diffuser includes a second plate, and wherein the diffuser vanes extend between the plate and the second plate.

15. The blower according to claim 14, wherein the diffuser vanes and the plate are integrally formed.

16. The blower according to claim 14, wherein the plate and the second plate are integrally formed.

17. The blower according to claim 1 wherein the blower includes multiple diffusers and multiple impellers.

\* \* \* \* \*